United States Patent [19]

Kikuchi

[11] Patent Number: 4,621,154
[45] Date of Patent: Nov. 4, 1986

[54] PROCESS FOR PREPARING 4-(4-BIPHENYLYL)-4-OXO-BUTANOIC ACID

[75] Inventor: Haruhiko Kikuchi, Kamifukuoka, Japan

[73] Assignees: Nisshin Flour Milling Co., Ltd.; Nisshin Chemicals Co., Ltd., both of Japan

[21] Appl. No.: 668,335

[22] Filed: Nov. 5, 1984

[30] Foreign Application Priority Data

Nov. 15, 1983 [JP] Japan ................................. 58-213403

[51] Int. Cl.$^4$ ............................................. C07C 59/86
[52] U.S. Cl. .................................................. 562/459
[58] Field of Search ......................................... 562/459

[56] References Cited

U.S. PATENT DOCUMENTS 3,859,363  1/1975  Teufel et al. ..................... 562/459
3,997,589 12/1976  Seeger et al. ..................... 562/459
4,058,558 11/1977  Cousse et al. ..................... 562/459

Primary Examiner—Paul J. Killos
Attorney, Agent, or Firm—Abelman Frayne Rezac & Schwab

[57] ABSTRACT

An improved process for preparing 4-(4-biphenylyl)-4-oxo-butanoic acid which is useful as anti-inflammatory and analgesic agents. The process comprises reacting biphenyl with succinic anhydride in chlorobenzene in the presence of anhydrous aluminum chloride. No 4-(4-chlorophenyl)-4-oxo-butanoic acid is produced as by-product.

7 Claims, No Drawings

PROCESS FOR PREPARING 4-(4-BIPHENYLYL)-4-OXO-BUTANOIC ACID

BACKGROUND OF THE INVENTION

This invention relates to a process for preparing 4-(4-biphenylyl)-4-oxo-butanoic acid useful as drugs and, more particularly, to an improved process for preparing the same by utilization of the Friedel-Crafts reaction in which chlorobenzene is used as a solvent.

4-(4-Biphenylyl)-4-oxo-butanoic acid is known to be a non-steroidal anti-inflammatory and analgesic agent having a low gastric disturbance, which is called "fenbufen" under a general name. As a process for the preparation of this compound, it is known that the process utilizing the Friedel-Crafts reaction is most effective. D. H. Hey, et al., in J. Chem. Soc. 1030 (1940) disclose the preparation of β-p-phenylbenzoylpropionic acid, by adding a mixture of diphenyl and succinic anhydride to a mixture of aluminum chloride and nitrobenzene at 5°–10° C., and standing the mixture for 6 days at room temperature. Likewise, Example 1 of U.S. Pat. No. 3,784,701 illustrates the preparation of 3-(4-biphenylcarbonyl)propionic acid, by dissolving aluminum chloride in nitrobenzene, adding a mixture of succinic anhydride and biphenyl to the solution at a temperature below 10° C., and holding the mixture at room temperature for 4 days. However, such prior art processes suffer from the disadvantages, either technical or economic in the point that nitrobenzene and sym-tetrachloroethane used therein as a solvent have high toxicity and high boiling point, and are more expensive than conventional solvents. In particular, high toxicity of the solvent has involved hazards in the handling thereof and troublesome waste water treating. They also suffer from the disadvantage of requiring long reaction time. Thus, there have been desired improved processes which can be carried out safely and in shorter reaction time.

SUMMARY OF THE INVENTION

It is a principal object of the present invention to provide a new process for preparing 4-(4-biphenylyl)-4-oxo-butanoic acid in an improved manner.

Another object of this invention is to provide a process for preparing 4-(4-biphenylyl)-4-oxo-butanoic acid in a safe and economical way.

These and other objects will become apparent from the following detailed discription.

It has now been surprisingly found that only 4-(4-biphenylyl)-4-oxo-butanoic acid can be prepared advantageously by reacting biphenyl with succinic anhydride in the presence of anhydrous aluminum chloride, using chlorobenzene of a low toxicity as a solvent. This finding is important to the development of this invention, since chlorobenzene has been expected to react with succinic anhydride in the presence of aluminum chloride to produce 4-(4-chlorophenyl)-4-oxo-butanoic acid (e.g., see Organic Reaction vol. 5, p. 263, 1949). According to the present invention, it is believed that chlorobenzene functions only as a solvent and does not substantially participate in the reaction with the result of no formation of the by-product 4-(4-chlorophenyl)-4-oxo-butanoic acid in any appreciable amount.

DESCRIPTION OF PREFERRED EMBODIMENTS

In general, the process of the present invention is directed to reacting in chlorobenzene biphenyl with succinic anhydride in the presence of anhydrous aluminum chloride whereby 4-(4-biphenylyl)-4-oxo-butanoic acid is obtained in good yield as an isolation product free of the by-product 4-(4-chlorophenyl)-4-oxo-butanoic acid having the formula

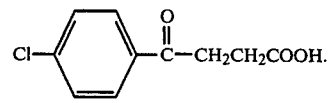

According to one embodiment of the present invention, there is provided a process for preparing 4-(4-biphenylyl)-4-oxo-butanoic acid of the formula

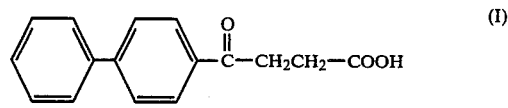

which comprises dissolving biphenyl of the formula

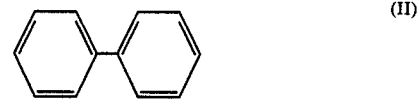

and succinic anhydride of the formula

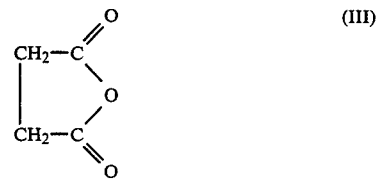

in chlorobenzene in amounts of from 5 to 10 times volume based on the weight of biphenyl, adding anhydrous aluminum chloride to the solution, heating and stirring the same.

In a preferred embodiment of the present invention, a molar ratio of biphenyl to succinic anhydride is advantageously 1:0.9–1.1, preferably 1:1–1.1. A molar ratio of biphenyl to anhydrous aluminum chloride is advantageously 1:2.0–3.0, preferably 1:2.2–2.5.

In the preferred embodiment of the present invention, the reaction is conducted at a temperature of between 100° C. and 120° C., and for 2 to 6 hours. If necessary, the reaction may be carried out at the reflux temperature of chlorobenzene.

This invention is further illustrated by the following examples, but not limited thereto.

EXAMPLE 1

To a solution of biphenyl (39.5 g., 0.257 mole) and succinic anhydride (25.6 g., 0.257 mole) dissolved in chlorobenzene (240 ml) is added anhydrous aluminum chloride (82.5 g., 0.616 mole). The mixture is elevated with stirring from room temperature up to 80° C. over 2 hours, and thereafter the reaction is performed at a temperature of 100°–110° C. for 4 hours. The reaction solution is cooled to 20° C., and the reaction product is decomposed with water (100 ml). Chlorobenzene is recovered by steam distillation and the residue is heated and dissolved with 5% aqueous solution of sodium hydroxide (300 ml). The alkali solution is filtered under heat, the filtrate is cooled, and the precipitated sodium salt of 4-(4-biphenylyl)-4-oxo-butanoic acid is removed by filtration. The resulting sodium salt is dissolved in hot water (300 ml), and 6N hydrochloric acid is added to the solution to provide 1–2 of pH, thus liberating the butanoic acid. The precipitated crystal is filtered, washed with water and dried under reduced pressure to give 48.0 g. (0.189 mole) of 4-(4-biphenylyl)-4-oxo-butanoic acid as white crystals, m.p. 187° C. (dec.)

NMR: $\delta_{TMS}^{DMSO\text{-}d_6}$ 2.60 (t, 2H), 3.30 (t, 2H), 7.35–8.10 (9H), 12.2 (b, 1H)

IR $\lambda_{max}^{cm^{-1}}$ (KBr): 2920, 2500–2800, 1700, 1670, 1600, 1400, 1240, 950

Mass (EI method): 254, 181, 153, 77

EXAMPLE 2

To a solution of biphenyl (40.0 g., 0.260 mole) and succinic anhydride (28.4 g., 0.284 mole) dissolved in chlorobenzene (360 ml) is added anhydrous aluminum chloride (80.1 g., 0.597 mole). The mixture is elevated with stirring from room temperature up to 80° C. over 2 hours, and thereafter the reaction is performed at 120° C. for 5 hours. The reaction solution is cooled to 20° C., and the reaction product is decomposed with water (100 ml). Chlorobenzene is recovered by steam distillation and the residue is heated and dissolved with 5% aqueous solution of sodium hydroxide (300 ml). The alkali solution is filtered under heat, the filtrate is cooled, and the precipitated sodium salt of 4-(4-biphenylyl)-4-oxo-butanoic acid is removed by filtration. The resulting sodium salt is dissolved in hot water (300 ml), and 6N hydrochloric acid is added to the solution to provide 1–2 of pH, thus liberating the butanoic acid. The precipitated crystal is filtered, washed with water and dried under reduced pressure to give 34.0 g. (0.134 mole) of 4-(4-biphenylyl)-4-oxo-butanoic acid as white crystals, m.p. 187° C. (dec.).

EXAMPLE 3

To a solution of biphenyl (30.0 g., 0.195 mole) and succinic anhydride (19.5 g., 0.195 mole) dissolved in chlorobenzene (180 ml) is added anhydrous aluminum chloride (68.2 g., 0.508 mole). The mixture is elevated with stirring from room temperature up to 80° C. over 2 hours, and thereafter the reaction is performed at 110° C. for 4 hours. The reaction solution is cooled to 20° C., and the reaction product is decomposed with water (100 ml). Chlorobenzene is recovered by steam distillation and the residue is heated and dissolved with 5% aqueous solution of sodium hydroxide (300 ml). The alkali solution is filtered under heat, the filtrate is cooled, and the precipitated sodium salt of 4-(4-biphenylyl)-4-oxo-butanoic acid is removed by filtration. The resulting sodium salt is dissolved in hot water (300 ml), and 6N hydrochloric acid is added to the solution to provide 1–2 of pH, thus liberating the butanoic acid. The precipitated crystal is filtered, washed with water and dried under reduced pressure to give 18.3 g. (0.072 mole) of 4-(4-biphenylyl)-4-oxo-butanoic acid as white crystals, m.p. 187° C. (dec.).

EXAMPLE 4

To a solution of biphenyl (100 g., 0.649 mole) and succinic anhydride (64.9 g., 0.649 mole) dissolved in chlorobenzene (600 ml) is added anhydrous aluminum chloride (174 g., 1.30 mole). The mixture is elevated with stirring from room temperature up to 80° C. over 2 hours, and thereafter the reaction is performed at 110° C. for 4 hours. The reaction solution is cooled to 20° C., and the reaction product is decomposed with water (300 ml). Chlorobenzene is recovered by steam distillation and the residue is heated and dissolved with 5% aqueous solution of sodium hydroxide (900 ml). The alkali solution is filtered under heat, the filtrate is cooled, and the precipitated sodium salt of 4-(4-biphenylyl)-4-oxo-butanoic acid is removed by filtration. The resulting sodium salt is dissolved in hot water (1000 ml), and 6N hydrochloric acid is added to the solution to provide 1–2 of pH, thus liberating the butanoic acid. The precipitated crystal is filtered, washed with water and dried under reduced pressure to give 58.7 g. (0.211 mole) of 4-(4-biphenylyl)-4-oxo-butanoic acid as white crystals, m.p. 187° C. (dec.).

EXAMPLE 5

To a solution of biphenyl (30.0 g., 0.195 mole) and succinic anhydride (19.5 g., 0.195 mole) dissolved in chlorobenzene (180 ml) is added anhydrous aluminum chloride (78.4 g., 0.585 mole). The mixture is elevated with stirring from room temperature up to 80° C. over 2 hours, and thereafter the reaction is performed at 120° C. for 4 hours. The reaction solution is cooled to 30° C., and the reaction product is decomposed with water (100 ml). Chlorobenzene is recovered by steam distillation and the residue is heated and dissolved with 5% aqueous solution of sodium hydroxide (300 ml). The alkali solution is filtered under heat, the filtrate is cooled, and the precipitated sodium salt of 4-(4-biphenylyl)-4-oxo-butanoic acid is removed by filtration. The resulting sodium salt is dissolved in hot water (250 ml), and 6N hydrochloric acid is added to the solution to provide 1–2 of pH, thus liberating the butanoic acid. The precipitated crystal is filtered, washed with water and dried under reduced pressure to give 5.0 g. (0.019 mole) of 4-(4-biphenylyl)-4-oxo-butanoic acid as white crystals, m.p. 187° C. (dec.).

What is claimed is:

1. A process for preparing 4-(4-biphenylyl)-4-oxo-butanoic acid which comprises reacting in chlorobenzene biphenyl with succinic anhydride in the presence of anhydrous aluminum chloride.

2. The process of claim 1 in which the reaction is carried out in a molar ratio of from 0.9 to 1.1 succinic anhydride to biphenyl.

3. The process of claim 1 in which the reaction is carried out in a molar ratio of from 2.0 to 3.0 anhydrous aluminum chloride to biphenyl.

4. The process of claim 1 in which the reaction is carried out by using from 5 to 10 times volume of chlorobenzene based on the weight of biphenyl.

5. The process of claim 1 in which the reaction is carried out at a temperature of from 100° C. to 120° C.

6. The process of claim 1 in which the reaction is carried out at the reflux temperature of chlorobenzene.

7. The process of claim 1 in which the reaction is carried out over a period from 2 hrs. to 6 hrs.

* * * * *